(12) United States Patent
Seifert

(10) Patent No.: US 10,772,743 B2
(45) Date of Patent: Sep. 15, 2020

(54) METHOD FOR CONTROLLING A CHANGE OF DAMPING IN AN ARTIFICIAL JOINT

(71) Applicant: OTTO BOCK HEALTHCARE PRODUCTS GMBH, Vienna (AT)

(72) Inventor: Dirk Seifert, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 304 days.

(21) Appl. No.: 15/569,038

(22) PCT Filed: Apr. 15, 2016

(86) PCT No.: PCT/EP2016/058356
§ 371 (c)(1),
(2) Date: Oct. 24, 2017

(87) PCT Pub. No.: WO2016/169850
PCT Pub. Date: Oct. 27, 2016

(65) Prior Publication Data
US 2018/0125681 A1 May 10, 2018

(30) Foreign Application Priority Data
Apr. 24, 2015 (DE) .......................... 10 2015 106 384

(51) Int. Cl.
*A61F 2/68* (2006.01)
*A61F 2/64* (2006.01)
(Continued)

(52) U.S. Cl.
CPC .................. *A61F 2/68* (2013.01); *A61F 2/64* (2013.01); *A61F 2/6607* (2013.01);
(Continued)

(58) Field of Classification Search
CPC ...... A61F 2/64; A61F 2/68; A61F 2002/5006; A61F 2002/5018; A61F 2002/502; B25J 9/0006; G05D 13/00
See application file for complete search history.

(56) References Cited

U.S. PATENT DOCUMENTS 6,423,098 B1 7/2002 Biedermann
6,719,806 B1 * 4/2004 Zahedi ...................... A61F 2/68
623/24

(Continued)

FOREIGN PATENT DOCUMENTS

CA 2779784 C 5/2011
CN 1498095 A1 5/2004
(Continued)

OTHER PUBLICATIONS

PCT International Search Report for PCT International Patent Application No. PCT/EP2016/058356, dated Jun. 17, 2016.

*Primary Examiner* — Bruce E Snow
(74) *Attorney, Agent, or Firm* — Holland & Hart, LLP

(57) ABSTRACT

A method for controlling a change of resistance in an artificial joint of an orthosis, an exoskeleton or prosthesis of a lower extremity. The artificial joint has an upper part and a lower part which are secured on each other so as to be pivotable about a pivot axis, a damper unit is secured between the upper part and the lower part in order to provide a resistance to flexion or extension of the artificial joint, and the damper unit is assigned an adjusting mechanism via which the resistance is changed when a sensor signal of a control unit assigned to the adjusting mechanism activates the adjusting mechanism. The resistance is changed as a function of the position and/or length of the measured or calculated leg tendon and/or the time derivatives thereof.

21 Claims, 4 Drawing Sheets

(51) Int. Cl.
    *G05D 13/00*    (2006.01)
    *A61F 2/66*    (2006.01)
    *A61F 5/01*    (2006.01)
    *A61F 2/50*    (2006.01)
    *A61F 2/70*    (2006.01)
    *A61F 2/76*    (2006.01)
    *A61F 2/74*    (2006.01)
    *A61H 3/00*    (2006.01)

(52) U.S. Cl.
    CPC .... *A61F 5/0125* (2013.01); *A61F 2002/5006* (2013.01); *A61F 2002/5033* (2013.01); *A61F 2002/6818* (2013.01); *A61F 2002/701* (2013.01); *A61F 2002/704* (2013.01); *A61F 2002/705* (2013.01); *A61F 2002/74* (2013.01); *A61F 2002/762* (2013.01); *A61F 2002/763* (2013.01); *A61F 2002/764* (2013.01); *A61F 2002/7625* (2013.01); *A61F 2002/7635* (2013.01); *A61F 2005/0188* (2013.01); *A61H 3/00* (2013.01)

(56) References Cited

U.S. PATENT DOCUMENTS

| | | |
|---|---|---|
| 6,755,870 B1 | 6/2004 | Biedermann et al. |
| 6,764,520 B2 | 7/2004 | Deffenbaugh et al. |
| 7,963,998 B2 | 6/2011 | Boiten |
| 9,603,724 B2 * | 3/2017 | Geyer ................. A61F 2/64 |
| 2003/0125814 A1 | 7/2003 | Paasivaara et al. |
| 2004/0193286 A1 | 9/2004 | Grundei |
| 2007/0123997 A1 | 5/2007 | Herr et al. |
| 2009/0171468 A1 | 7/2009 | Pusch et al. |
| 2011/0087339 A1 | 4/2011 | Pusch et al. |
| 2012/0221120 A1 | 8/2012 | Seyr et al. |
| 2012/0226364 A1 | 9/2012 | Kampas et al. |
| 2015/0018972 A1 | 1/2015 | Albrecht-Laatsch |

FOREIGN PATENT DOCUMENTS

| | | |
|---|---|---|
| CN | 101389291 A | 3/2009 |
| CN | 102793596 A | 11/2012 |
| CN | 103271783 A | 9/2013 |
| CN | 104244872 A1 | 12/2014 |
| DE | 102006021802 A1 | 11/2007 |
| DE | 102008008284 A1 | 8/2009 |
| DE | 102009052887 A1 | 5/2011 |
| DE | 102012003369 A1 | 8/2013 |
| EP | 1447062 A2 | 8/2004 |
| JP | 2002-533161 A | 10/2002 |
| JP | 2013-510605 A | 3/2013 |
| RU | 2294715 C2 | 3/2007 |
| RU | 2505272 C1 | 1/2014 |
| WO | 2011057793 A1 | 5/2011 |

* cited by examiner

METHOD FOR CONTROLLING A CHANGE OF DAMPING IN AN ARTIFICIAL JOINT

TECHNICAL FIELD

The invention relates to a method for controlling a change in resistance in an artificial joint of an orthosis, of an exoskeleton or prosthesis of a lower extremity, wherein the artificial joint has an upper part and a lower part which are fastened to one another pivotably about a pivot axis, wherein a resistance unit is fastened between the upper part and the lower part in order to provide a resistance to flexion or extension of the artificial joint, and the resistance unit is assigned an adjustment device by means of which the resistance is changed if a sensor signal of a control unit assigned to the adjustment device activates the adjustment device. The method is used in particular for the control of the movement or damping behavior of artificial knee joints, but is not restricted to this, and may also be used for hip or ankle joints.

BACKGROUND

Artificial joints for orthoses, exoskeletons or prostheses have an upper part with an upper connection part and a lower part with a lower connection part, which are articulatedly connected to one another. In general, in the case of artificial knee joints, receptacles for a thigh stump or a thigh rail are arranged on the upper connection part, whereas a lower leg tube or a lower leg rail with a prosthetic foot or a foot part are arranged on the lower connection part. In the case of a lower leg still being present, the upper part of a prosthesis is arranged on a lower leg socket, the prosthetic foot is fastened to the lower part, and in the case of orthoses, the respective components are fastened to the associated limbs. In the simplest case, the upper part and the lower part are connected pivotably to one another by means of a uniaxial joint.

To be able to satisfy or support different requirements during the different phases of a step or during other movements or actions in a way that is as natural as possible, a resistance device is often provided which provides flexion resistance and extension resistance. The flexion resistance is used for setting how easily the lower part can be pivoted in relation to the upper part when a force is applied. In the case of a knee joint, the extension resistance brakes the forward movement of the lower part and forms, inter alia, an extension limit stop, and the flexion resistance prevents undesired flexion and limits the maximum flexion in the swing phase.

DE 10 2008 008 284 A1 has disclosed an orthopedic knee joint with an upper part and with a lower part arranged pivotably thereon, which lower part is assigned multiple sensors, for example a flexion angle sensor, an acceleration sensor, an inclination sensor and/or a force sensor. The position of the extension stop is determined in a manner dependent on the sensor data.

DE 10 2006 021 802 A1 describes control of a passive prosthetic knee joint with adjustable damping in a flexion direction for adaptation of a prosthesis device with top-side connection means and with a connecting element to an artificial foot. The adaptation is made to climbing stairs, wherein a low-moment lifting of the prosthetic foot is detected, and the flexion damping is, in a lifting phase, lowered to below a level suitable for walking on a level surface. The flexion damping may be increased in a manner dependent on the change in the knee angle and in a manner dependent on the axial force acting on the lower leg.

DE 10 2009 052 887 A1 describes, inter alia, a method for controlling an orthotic or prosthetic joint with a resistance device and with sensors, wherein items of state information are provided by means of sensors during the use of the joint. The sensors detect moments or forces, wherein the sensor data of at least two of the determined variables are linked to one another by means of a mathematical operation, and in this way an auxiliary variable is calculated which is used as a basis for the control of the flexion and/or extension resistance.

According to the prior art, for the control of the change in the damping behavior, the sensor data are evaluated quantitatively, that is to say, in general, certain threshold values are predefined, in the case of the attainment or non-attainment of which the actuator is activated or deactivated, such that the resistance device provides an increased or reduced flexion or extension resistance.

Patients may use prostheses, exoskeletons or orthoses in various environments. They may walk down stairs, walk down ramps or walk on a level surface at various speeds. Furthermore, loads may be carried, which likewise has an effect on the behavior of the prosthesis or orthosis. In particular after the end of the swing phase, that is to say after the setting-down of the aided leg, when the body weight is shifted onto the aided leg, there is often a requirement for increased safety for the patient. Excessively high initial flexion damping, that is to say damping which counteracts flexion of the artificial knee joint, would however lead to a shock load in the hip joint, which would result in a reduction in wearing comfort and acceptance of the prosthesis or orthosis.

Modern computer-controlled damping devices are capable of adapting the resistance to flexion or extension in a very precise and rapid manner. Limiting factors are the accuracy of the determined or detected data, the complexity of the information to be processed, the reliability of the detection of the movement respectively being performed, and the outlay in terms of construction.

SUMMARY

It is an object of the present invention to provide a method for controlling an artificial joint of a lower extremity, in particular an artificial knee joint, with which reliable, rapid and inexpensive adaptation to different walking situations and comfortable walking behavior can be achieved with simultaneously maximum safety.

According to the invention, said object is achieved by means of a method having the features of the main claim. Advantageous embodiments and refinements of the invention are disclosed in the subclaims, in the description and in the figures.

The method according to the invention for controlling a change in damping in an artificial joint of an orthosis, of an exoskeleton or prosthesis of a lower extremity, wherein the artificial joint has an upper part and a lower part which are fastened to one another pivotably about a pivot axis, wherein a resistance unit is fastened between the upper part and the lower part in order to provide a resistance to flexion or extension of the artificial joint, and the resistance unit is assigned an adjustment device by means of which the resistance is changed if a sensor signal of a control unit assigned to the adjustment device activates the adjustment device, provides that the resistance is changed in a manner dependent on the position and/or length of the leg chord and/or the derivatives thereof with respect to time. The leg chord is thus used as a control parameter or auxiliary variable for the purposes of identifying, on the basis of the position or length, or a combination of position and length, of the leg chord, the movement that is presently being performed, such that the required changes in resistance for the respective walking situation or other activities such as sitting down, standing up, bicycle riding, walking backwards or the like can be suitably initiated. The position of the leg chord provides reliable information regarding the orientation of the leg independently of a flexion, for example a stance phase flexion or stance phase extension. Furthermore, from the position of the leg chord and a shortening of the leg chord without a change in position, it is possible to infer a stationary leg-bending movement; a forward rotation of the leg chord indicates walking down a ramp; and a backward rotation indicates for example a sitting-down movement. On the basis of the evaluation of these items of information, the control unit activates the adjustment device in order to adapt the resistance in the resistance unit to the respective walking situation. For this purpose, flexion and extension resistance are suitably increased or decreased. The length of the leg chord furthermore allows conclusions to be drawn regarding the progress of movement; for example, if the leg chord shortens during a backward rotation, it is possible from this to detect or at least estimate the progress of a sitting-down movement. An adaptation of the resistance is correspondingly performed on the basis of this information. The derivatives with respect to time of the position or length of the leg chord are likewise relevant. The speeds or accelerations of the respective movement are determined, which provides indications for example of a walking speed, such that correspondingly changed resistance values are provided in the respective movement phases. The method is directed not only to the control of resistance units in artificial knee joints; it is rather also possible in damped ankle joints for a corresponding resistance unit to be changed in a manner dependent on the length and/or position of the leg chord or the derivatives with respect to time thereof. The same also applies to a resistance unit in a hip joint. The method may be used in an orthosis, prosthesis or in a special form of orthosis, specifically an exoskeleton.

As a leg chord, use is preferably made of the connecting line between a hip center of rotation and a foot point. In the case of a prosthetic knee joint, the hip center of rotation is determined for example by an orthopedic technician. The hip center of rotation also defines the segment length of the thigh, which is defined as the spacing between the pivot axis or knee axis and the hip center of rotation. The lower leg length is defined between the knee axis and a foot point. Either the foot center, the instantaneous center of rotation of a rolling movement, or the end point of the vertical line of the lower leg at the sole level of the foot part, of the prosthetic foot or on the ground may be defined as the foot point. In the case of orthoses or exoskeletons, a foot part for the support of a natural foot that is still present is not imperatively required if the control of a resistance unit between a thigh part and a lower leg part is to be performed.

The position of the leg chord, or the leg chord angle, may be estimated as a sum of a determined lower leg angle and of a knee angle multiplied by a factor. The factor lies in a range between 0.4 and 0.6, and the position of the leg chord with respect to the vertical is advantageously estimated from the sum of the lower leg angle with respect to the vertical and the halved knee angle. Alternatively, the position of the leg chord may be calculated from the lower leg angle, the knee angle and the thigh segment length with the lower leg segment length. The respective segment lengths are known and are stored in the control device. The lower leg angle may be determined by means of position sensors; the knee angle, which indicates the relative pivoting about the knee axis, is defined as the angle between the projection of the longitudinal extent of the lower leg and the longitudinal extent of the thigh; the measurement may be performed by means of an angle sensor.

The lower leg angle and/or the thigh angle may be directly measured by means of an inertial angle sensor. Alternatively, an position sensor may be arranged on the respective other segment, wherein the knee angle is determined by means of a knee angle sensor, and the thigh angle is determined from a combination of the inertial angle of the thigh with the knee angle of the lower leg angle or from a combination of an position sensor on the lower leg and the knee angle sensor.

The length of the leg chord may be determined from the knee angle and the segment lengths of thigh and lower leg. From the length of the leg chord or the change thereof with respect to time, conclusions can be drawn regarding movement speeds, in a manner dependent on which the resistances in the damping unit are changed.

The resistance in the resistance unit may also be changed in a manner dependent on the direction of the change in the position and/or length of the leg chord. Accordingly, a forward rotation may be detected by means of a reduction of the leg chord angle in the direction of a vertical, or an increase of the leg chord angle away from the vertical may be detected as a yielding step when walking down a ramp, in particular if the leg chord length shortens. The shortening or lengthening of the leg chord provides an indication as to whether a standing-up or a sitting-down movement, a leg-bending or standing movement or walking down stairs or walking up stairs is being performed.

In the case of walking forwards, that is to say in all walking situations in which forward progression occurs, the leg rolls forwards. The leg orientation, that is to say the orientation of the leg chord, and the change in said orientation can thus be regarded as progression parameters for a step. After the heel strike, the leg normally has a backward inclination, that is to say the leg chord is inclined backward relative to the vertical, counter to the walking direction. The leg subsequently rolls forward; the leg chord angle decreases in the direction of the vertical and then increases proceeding from the vertical until a maximum forward inclination is present at the end of the stance phase. For a more precise distinction of the walking situation, it is advantageous for a quotient of the change in the position of the leg chord and the change in the thigh angle or lower leg angle to be determined and used for the assessment of the walking situation. The thigh angle or lower leg angle or the derivatives thereof with respect to time correlate with the movement of the leg during the step. During forward walking on a level surface, the thigh and the lower leg likewise roll forward; this occurs both with and without stance phase flexion. During walking down ramps, the thigh angle remains approximately constant; when walking down stairs, the thigh tilts rearward, and the angle thus increases relative to the vertical. Depending on the determined walking situation, the resistance is then adapted; for example, the flexion damping is increased or decreased for a particular angle range in order to permit flexion during alternating walking down stairs.

In particular, a quotient of the change in the position of the leg chord and the change in the thigh angle or in the lower leg angle may be determined and used as a parameter for the identification of the walking situation. In particular, the resistance may be changed in a manner dependent on the gradient of the graph of the respective phase diagram. If the thigh angle or lower leg angle is plotted versus the leg chord position or the leg chord angle, walking situations can be distinguished on the basis of the gradient in the phase diagram. The gradient may be determined as or from a differential quotient $\Delta\varphi_i/\Delta\varphi_j$ or the differential quotient $d\varphi_i/d\varphi_j$ of the functional relationship of two angles $\varphi_i$ and $\varphi_j$, wherein, for example, the present tangent or else the secant over a longer time period may be considered. The behavior of the resistance unit may be adapted to the corresponding situations in a manner dependent on the gradient.

Aside from the change in the resistance unit or in the resistance on the basis of the gradient in the phase diagram of the angle, provision is likewise made for said change in the resistance to also be performed on the basis of a quotient of the derivatives thereof with respect to time, specifically from the quotient of the change in the leg chord speed and the change in the thigh speed or lower leg speed.

The distinction of the various walking situations can be made even more precise in that, for the detection of the stance phase or of standing, a force sensor is used which detects an axial force acting on the lower part or a moment acting on the lower part. If the lower part is unloaded or substantially unloaded, it can be assumed that the lower extremity is in the swing phase, lifting phase or setting-down phase, which requires a different setting of the resistances than standing or the stance phase during walking. A corresponding sensor can provide the additional information in this regard.

The resistance is advantageously changed additionally in a manner dependent on the position and/or the change in position of the upper part and/or of the lower part. The upper part and lower part advantageously act as thigh and lower leg. The resistance is preferably changed in particular if the position and/or the change in position of the leg chord overshoots or undershoots a predetermined threshold value.

It is self-evidently possible for the position to be changed in a manner dependent on all of said stated parameters or only some of the stated parameters.

The resistance unit may for example be configured as an actuator, for example as a hydraulic, pneumatic, magnetorheological, magnetic, electrical, mechanical or electromagnetic resistance unit. In the case of hydraulic or pneumatic resistance units, flow transfer channels are closed, such that said flow transfer channels can no longer allow medium to flow from an extension chamber into a flexion chamber. In this way, the flow of the medium between the extension chamber and the flexion chamber can possibly also be prevented entirely. In the case of mechanical resistance devices, it is for example the case that the friction is increased to such an extent that no further flexion is possible. The same applies to electrically actuated resistance units.

Use may also be made of actuators which both actively introduce energy into the system and also conversely extract energy from the system, and thereby act as a resistance unit. Actuators may for example be formed as electric motors, hydraulic or pneumatic pumps or piezoelectric elements.

BRIEF DESCRIPTION OF THE DRAWINGS

Exemplary embodiments of the invention will be discussed in more detail below on the basis of the appended figures. In the figures.

DETAILED DESCRIPTION

Figure 1:
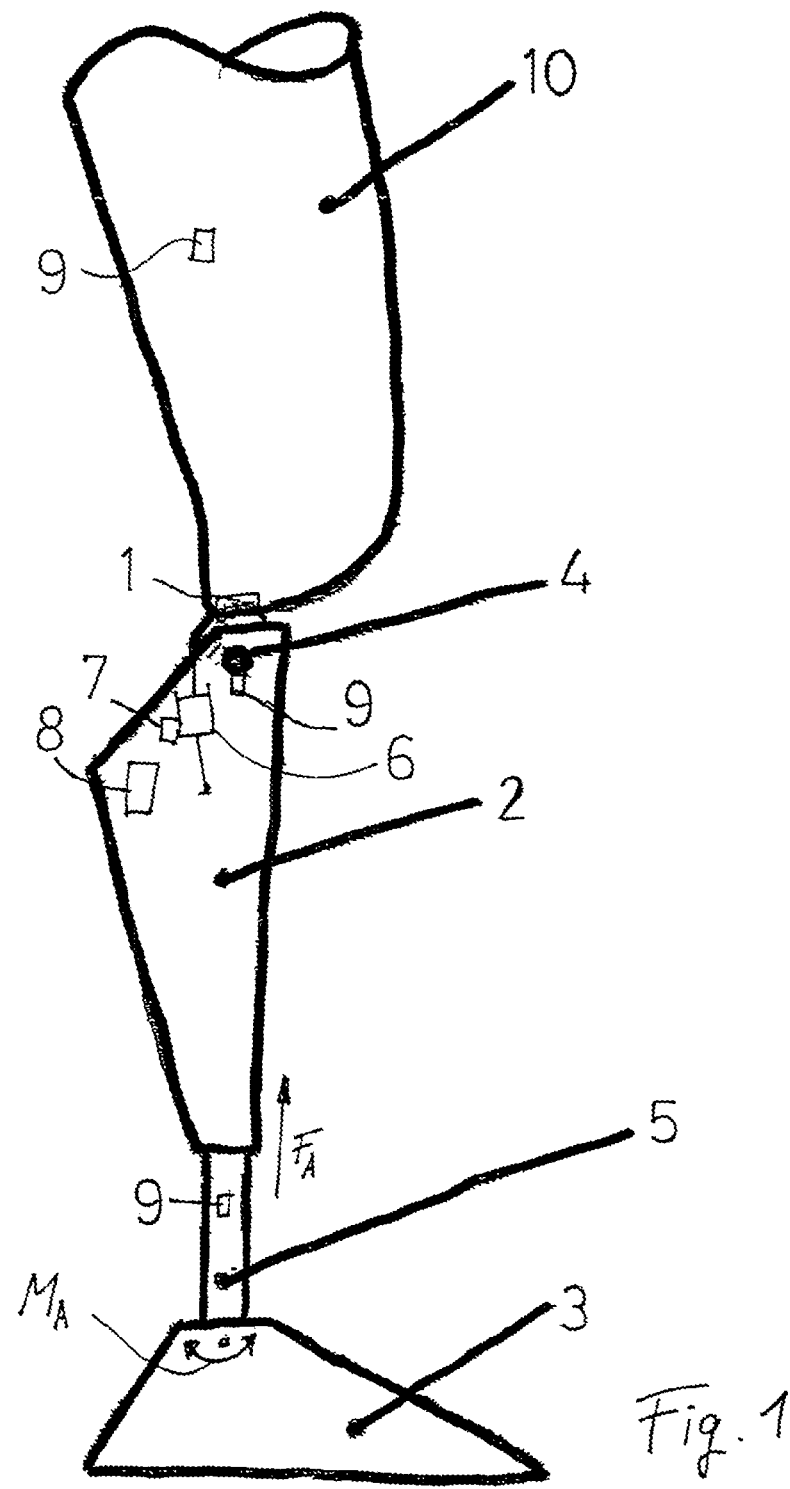
FIG. 1—shows a schematic illustration of a leg prosthesis,
FIG. 2—shows a schematic illustration of a knee prosthesis with angles.

FIG. 1 shows, in a schematic illustration, a leg prosthesis with an upper part 1 to which a thigh socket 10 for receiving a thigh stump is fastened. A lower part 2 designed as a lower leg part is arranged pivotably on the upper part 1. The lower part 2 is mounted on the upper part 1 pivotably about a pivot axis 4. The lower part 2 has a lower leg tube 5, to the distal end of which there is fastened a prosthetic foot 3 in which there may be accommodated a device for determining the axial force acting on the lower leg tube 5 and the ankle moment acting about the fastening point of the prosthetic foot 3 to the lower leg tube 5.

In or on the lower part 2 there is arranged a resistance device 6 which may be formed for example as a damper or actuator and which is supported between the upper part 1 and the lower part 2 in order to provide an adjustable extension resistance and flexion resistance. The resistance device 6 is assigned an adjustment device 7, for example a motor, a magnet or some other actuator, by means of which the respective resistance R within the resistance unit 6 can be varied. If the resistance unit 6 is formed as a hydraulic damper or pneumatic damper, it is possible by means of the adjustment device 7 for the respective flow cross section of a flow transfer channel to be increased or decreased in size. It is likewise possible for the flow resistance to be varied in some other way by means of the adjustment device 7. This may be realized for example by opening or closing valves or changing viscosities or magnetorheological characteristics. If the resistance unit is formed as an electric motor operating as a generator, it is possible for an increase or decrease in the respective resistances to flexion or extension to be set through variation of the electrical resistance. The resistance unit may also be formed as a mechanical resistance to flexion or extension, as a friction brake or as an elastomer element with variable deformation resistance or a magnetorheological damper.

To be able to activate or deactivate the adjustment device 7, a control device 8 is assigned to the lower part 2, in particular is accommodated in a lower leg trim, by means of which control device a corresponding activation or deactivation signal is output to the adjustment device 7. The adjustment device 7 is activated or deactivated on the basis of sensor data, and the sensor data are provided by one or more sensors 9 which are arranged on the artificial knee joint. These may be angle sensors, inertial angle sensors, acceleration sensors and/or force sensors. The sensors 9 are connected to the control device 8, for example by cable or by means of a wireless transmission device. In the exemplary embodiment illustrated, the sensor 9 is formed inter alia as a knee angle sensor or inertial angle sensor. The sensors may be arranged on the thigh socket 10, on the upper part 1, on the lower part 2, on the lower leg tube 5 or on the foot part 3. In the case of orthoses, the sensors are fastened to the respectively corresponding rails, joint parts or foot parts; the sensors 9 may also be fastened to the limbs themselves.

The entire step cycle from the heel strike via toe lift-off to the new, next heel strike HS, and thus also the entire swing phase with the swing phase extension and the swing phase flexion, is monitored by means of the sensors 9.

Figure 2:
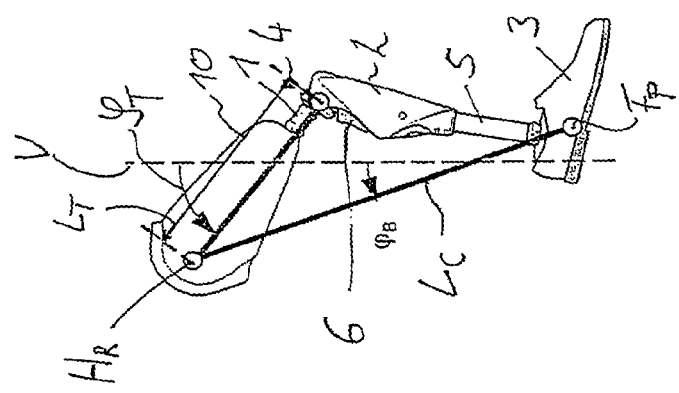

FIG. 2 shows, in a side view, a prosthetic knee joint with the thigh socket 10, the upper part 1, the lower part 2 which is mounted pivotably about a knee axis 4 and which has the resistance unit 6 arranged therein, the distal lower leg tube 5, and the prosthetic foot fastened to the latter, in a flexed position. The leg chord $L_C$ extends between a foot point $F_P$ and a hip center of rotation $H_R$. The leg chord $L_C$ is the connection between the hip center of rotation $H_R$ and the foot point $F_P$; by means of the orientation of the leg chord $L_C$, conclusions can be drawn regarding the movement presently being performed, and in particular, different movements or walking situations can be distinguished from one another. The foot point $F_P$ may be situated in the center of the foot; an alternative definition of the foot point $F_P$ is the instantaneous center of rotation of the polar movement, the pivot axis of the ankle joint or the projection of the longitudinal extent of the lower part 2 to the level of the sole of the foot. Shown as a characteristic variable for the position of the leg chord $L_C$ is the leg chord angle $\varphi_B$, which is defined as the angle between the leg chord $L_C$ and a vertical V. In the illustrated position of the prosthesis device, the upper part 1 is flexed relative to the lower part 2 by an angle; the leg chord $L_C$ is thus tilted in the rearward direction. As a result, there is also a thigh angle $\varphi_T$ relative to the vertical V. The thigh angle $\varphi_T$ increases relative to the vertical V if, for example, the lower part 2 remains vertical and the upper part 1 is pivoted counterclockwise in the illustrated exemplary embodiment about the pivot axis 4. A reference variable for the thigh angle $\varphi_T$ is the connecting line between the hip center of rotation $H_R$ and the knee axis 4; the distance between the two points along said connecting line simultaneously defines the thigh length $L_T$.

Figure 3:
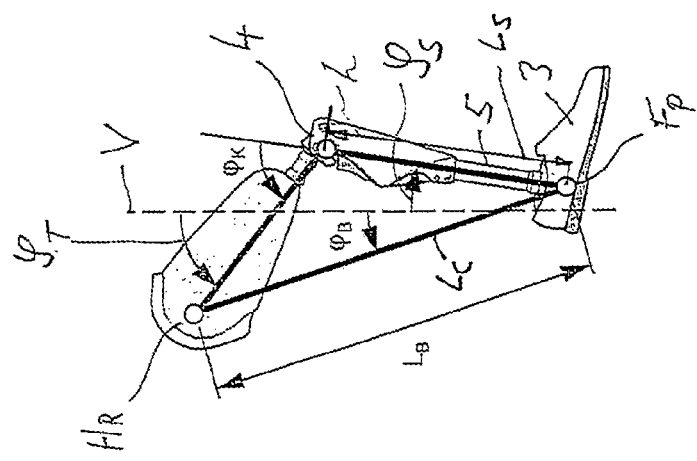
FIG. 3—shows an illustration as per FIG. 2 with parameter assignment.

In FIG. 3, in addition to the variables in FIG. 2, the knee angle $\varphi_K$ is plotted, which is the angle between the thigh segment, represented by the connecting line between the knee axis 4 and the hip center of rotation $H_R$, and the longitudinal extent of the lower part 2. The knee angle $\varphi_K$ is 0 if the prosthesis device is in a maximally extended position. This means that the longitudinal extent of the lower part 2 is aligned with the longitudinal extent of the upper part 1, that is to say the connection between the knee axis 4 and the hip center of rotation $H_R$ is aligned with the connecting line between the knee axis 4 and the foot point $F_P$ if the latter lies on the axis of the longitudinal extent of the lower leg tube 5.

The lower leg length Ls is defined by the spacing between the knee axis 4 and the foot point $F_P$. The lower leg angle $\varphi_S$ is the angle between the vertical V and the connecting line between the foot point $F_P$ and the knee axis 4. In the illustrated exemplary embodiment with the prosthetic knee joint flexed by an angle $\varphi_K$, the lower leg angle $\varphi_S$ is tilted positively in a forward walking direction, the thigh angle $\varphi_T$ is oriented in the backward direction relative to the vertical, and the leg chord $L_C$ is tilted backward by the angle $\varphi_B$. The length $L_B$ of the leg chord $L_C$ is defined by the spacing between the hip center of rotation $H_R$ and the foot point $F_P$.

The length $L_B$ of the leg chord $L_C$ can be calculated from the known segment lengths $L_T$ and Ls in conjunction with the knee angle. In addition to inertial angle sensors 9 which may be arranged on the lower part 2 or the upper part 1 or the thigh socket 10 or the lower leg tube 5, the orientation or the leg chord angle $\varphi_B$ may also be estimated from a combination of the lower leg angle $\varphi_S$ in conjunction with a weighted knee angle $\varphi_K$, wherein the formula for this is $$\varphi_B = \varphi_S + d \times \varphi_K,$$

where d lies between 0.4 and 0.6, and is in particular 0.5.

With the knowledge of the length $L_B$ and orientation $\varphi_B$ of the leg chord $L_C$ and possibly the derivatives with respect to time of said variables, it is possible to follow the rolling movement in the stance phase independently of stance phase flexion or stance phase extension, and to obtain knowledge regarding the progression of the movement. By means of the change in the leg chord orientation or in the leg chord angle $\varphi_B$, the movement progression can be followed both in the stance phase and in the swing phase, such that said variable can be taken into consideration for the control of the stance phase behavior and/or swing phase behavior through adaptation of the damper settings.

The thigh angle $\varphi_T$ and also the lower leg angle $\varphi_S$, which can also be referred to as segment angles, may be measured by means of inertial sensors which are situated on the respective segment. Alternatively, a calculation is performed by means of only one inertial sensor on the segment not involved in each case and the knee angle $\varphi_K$, which is determined by means of a knee angle sensor.

Figure 4C:
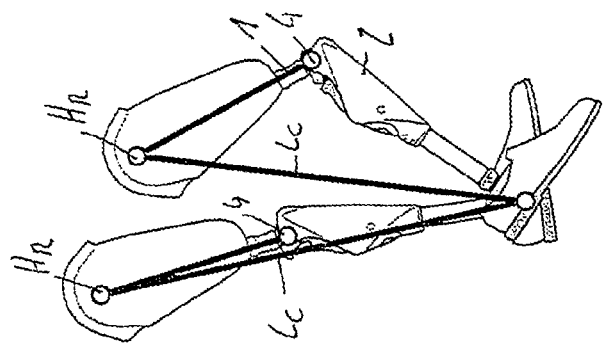
FIGS. 4*a*-4*c*—show illustrations of different situations during walking.
Figure 4B:
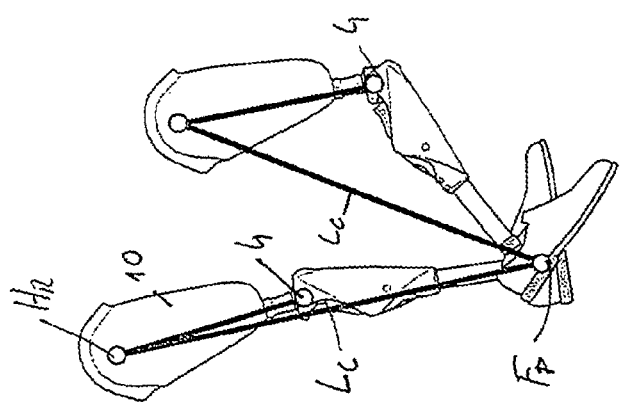
Figure 4A:
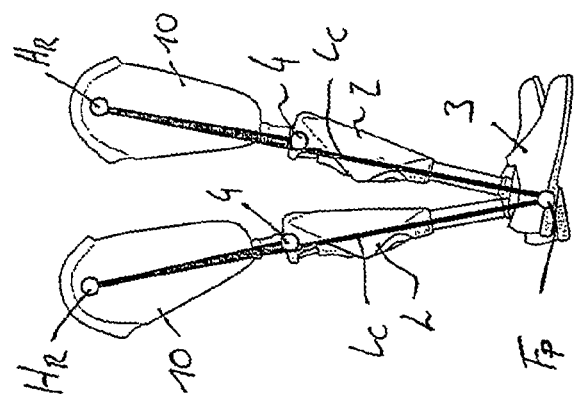

FIG. 4a shows two sections of a leg position for walking on a level surface. The left-hand illustration shows the prosthesis device shortly after the heel strike; the length $L_B$ of the leg chord $L_C$ is approximately at a maximum, because the leg chord angle (not shown) $\varphi_B$ approximately corresponds to the thigh angle $\varphi_S$. During the further course of the step, a forward progression occurs, the prosthesis device as a whole rotates forward, and the leg chord $L_C$ is pivoted forward about the foot point $F_P$, which may also be situated in an ankle joint, such that the leg chord $L_C$ is situated in front of the vertical. It can be seen from FIG. 4a that, over the major part of the forward progression when walking on a level surface, the thigh or thigh socket 10 is jointly displaced forward together with the leg chord $L_C$ in the case of an approximately extended knee joint, and a change in the knee angle does not occur.

FIG. 4b shows walking on a downwardly directed ramp. The left-hand illustration shows increased flexion in the prosthetic knee joint, the thigh socket 10 has been pivoted about the knee axis 4, and the orientation of the leg chord $L_C$ corresponds approximately to that in the setting-down phase when walking on a level surface.

The further profile of the movement when walking down a ramp is shown in the right-hand illustration of FIG. 4b. A rolling movement about the foot point $F_P$ likewise occurs, the leg chord $L_C$ rotates forward about the foot point $F_P$, and the thigh angle $\varphi_S$ remains in a virtually constant position owing to increased flexion about the knee axis 4, that is to say the orientation of the thigh or thigh socket 10 in space does not change, or changes only insignificantly, while the leg chord $L_C$ performs a forward rotation.

A third walking situation, specifically walking down stairs, is illustrated in FIG. 4c. The position of the individual components of the prothesis device corresponds, in the initial position shown in the left-hand illustration, to walking down a ramp. The leg chord $L_C$ is inclined backward, that is to say is tilted backward counterclockwise relative to the vertical. During the further course of alternating walking down stairs, the prosthesis device is flexed, pivoting of the upper part 1 relative to the lower part 2 occurs, the knee angle $\varphi_K$ increases, and likewise, the length $L_P$ of the leg chord $L_C$ decreases. The orientation of the leg chord $L_C$ changes less than when walking on a level surface or when walking down a ramp, that is to say a forward rotation of the leg chord $L_C$ occurs only to a relatively small extent, and the leg chord angle $\varphi_B$ relative to the vertical is thus smaller than in the case of walking on a level surface or walking down a ramp.

In the walking situations in FIGS. 4a to 4c, forward progression occurs, that is to say the leg rolls forward. A suitable parameter or an auxiliary variable for distinguishing and detecting the respective walking situation is the quotient between the change in the thigh angle $\varphi_T$ or in the lower leg angle $\varphi_S$ and the change in the leg orientation or in the leg chord angle $\varphi_B$. Likewise, the derivatives with respect to time are suitable and provided as characteristic variables, that is to say the quotient of the change in the angular speeds of the leg chord $L_C$ and of the thigh or the lower leg.

Figure 5:
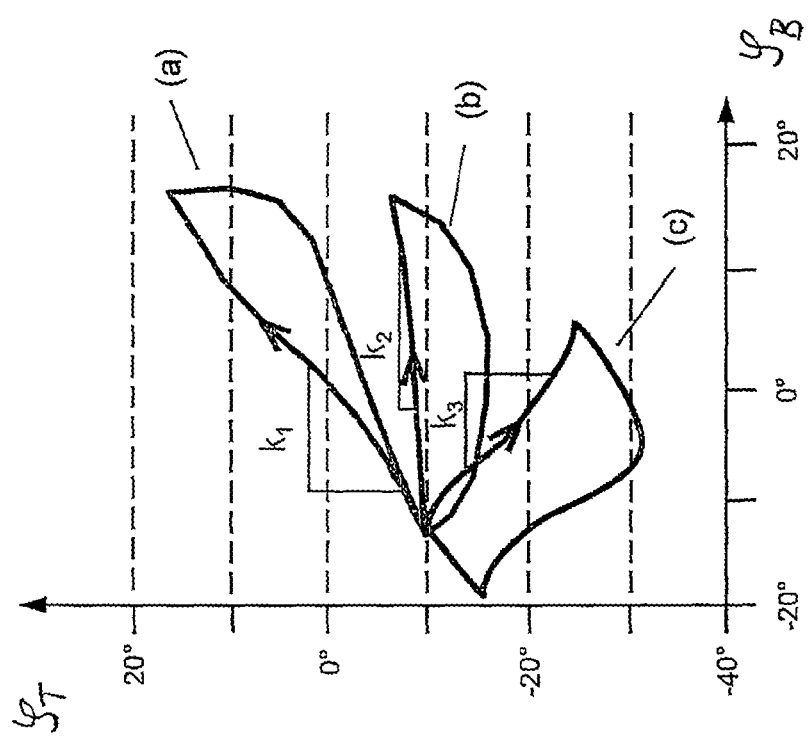
FIG. 5—shows various illustrations of a thigh angle versus the leg orientation.

The profiles of the respective angles are plotted in FIG. 5; curve a shows the profile of the angle for walking on a level surface, curve b shows the profile of the leg chord and thigh angles for walking down a ramp, and curve c shows the profile of the angle for walking down stairs.

It is clear that all curves a, b, c have a different profile, and in particular, the gradient k differs for the respective curve profile. The gradient k can be determined as a differential quotient; the formula for this is $$k=(\varphi_{T1}-\varphi_{T0})/(\varphi_{B1}-\varphi_{B0})$$

The gradient $k_1$ for walking on a level surface is much steeper than the gradient $k_2$ for walking down a ramp. Whereas, in the case of walking on a level surface as per curve a, the change in the thigh angle $\varphi_T$ is substantially aligned with the change in the leg chord angle $\varphi_B$, and the gradient is approximately 1, the thigh angle $\varphi_T$ when walking down a ramp is approximately constant, such that a much shallower gradient $k_2$ is realized for walking down a ramp. In the case of walking down stairs, the leg chord angle $\varphi_B$ decreases to a much lesser extent than the thigh angle $\varphi_T$, such that the gradient $k_3$ when walking down stairs assumes a negative value.

In a manner dependent on the detected quotients or the respective gradient $k_1$, $k_2$, $k_3$, an adaptation of the resistances can be performed; in the case of walking down a ramp being detected as per curve profile b, the standard setting for walking on a level surface may be changed such that yielding occurs, and thus reduced flexion is present at a corresponding leg chord angle $\varphi_B$. If a negative gradient $k_3$ as per curve c in FIG. 5 is detected, it can be assumed that walking down stairs is being performed. A slow leg-bending movement or the prevention of a complete lock-up of the prosthesis device should be avoided in order to prevent a catapult effect.

Correspondingly characteristic phase diagrams are obtained if, instead of the angles, the angular speeds or angular accelerations of leg chord and thigh or lower legs are plotted.

With the method according to the invention, no forces or force profiles need to be measured or evaluated in order to make a distinction between walking situations and the movement progression thereof. It is basically the case that only angles are measured, calculated or estimated and used as a basis for the change in the damper setting.

The invention claimed is:

1. A method for controlling a change in resistance in an artificial joint of an orthosis, an exoskeleton, or prosthesis of a lower extremity, the method comprising:
providing an artificial joint having an upper part and a lower part which are fastened to one another pivotably about a pivot axis, a resistance unit fastened between the upper part and the lower part in order to provide a resistance to flexion or extension of the artificial joint, the resistance unit being assigned an adjustment device operable to change the resistance if a sensor signal of a control unit assigned to the adjustment device activates the adjustment device;
changing the resistance in a manner dependent on at least one of a position and length of at least one of a measured or calculated leg chord and derivatives thereof with respect to time, the leg chord being a connecting line between a hip center of rotation and a foot point, the hip center of rotation and the foot point being fixed relative to the upper part and the lower part, respectively.

2. The method as claimed in claim 1, wherein a connecting line between a hip center of rotation and a foot point is used as the leg chord.

3. The method as claimed in claim 1, wherein the position of the leg chord is estimated as a sum of a lower leg angle and a fraction of a knee angle, or is calculated using the lower leg angle, the knee angle, a thigh segment length and a lower leg segment length.

4. The method as claimed in claim 1, wherein the lower leg angle or thigh angle is directly measured using an inertial angle sensor, or is determined using an position sensor on a thigh or lower leg and a knee angle sensor.

5. The method as claimed in claim 3, wherein the length of the leg chord is determined from the knee angle and the thigh and lower leg segment lengths.

6. The method as claimed in claim 1, wherein the resistance is changed in a manner dependent on a direction of a change in at least one of the position andthe length of the leg chord.

7. The method as claimed in claim 1, wherein a quotient is determined from a change in a position of the leg chord and a change in a thigh angle or lower leg angle, the quotient being used for an assessment of the walking situation.

8. The method as claimed in claim 1, wherein a quotient is determined from a change in a leg chord speed and a change in a thigh speed or a lower leg speed, the quotient being used for an assessment of the walking situation.

9. The method as claimed in claim 8, wherein a force sensor for detecting forces in the lower part detects a stance phase or standing.

10. The method as claimed in claim 1, wherein the resistance is changed additionally in a manner dependent on a position or change in position of at least one of the upper part and the lower part.

11. The method as claimed in claim 1, wherein the resistance is changed if at least one of a position and a change in position of the leg chord overshoots or undershoots a predetermined threshold value.

12. A method for controlling a change in resistance in an artificial joint of an orthosis, an exoskeleton, or prosthesis of a lower extremity, the method comprising:
providing an artificial joint having an upper part, a lower part, a resistance unit, and an adjustment device, the upper part being pivotally connected to the lower part, the resistance unit providing a flexion resistance or an extension resistance, the adjustment device including a control unit, the adjustment device being operable to change the flexion resistance or extension resistance if a sensor signal of the control unit activates the adjustment device;
changing the flexion resistance or extension resistance based on a position and a length of a measured or calculated leg chord and derivatives thereof with respect to time, the leg chord being a connecting line between a hip center of rotation and a foot point, the hip center of rotation and the foot point being fixed relative to the upper part and the lower part, respectively.

13. The method as claimed in claim 12, wherein a connecting line between a hip center of rotation and a foot point is used as the leg chord.

14. The method as claimed in claim 12, wherein the position of the leg chord is estimated as a sum of a lower leg angle and a fraction of a knee angle, or is calculated using the lower leg angle, the knee angle, a thigh segment length, and a lower leg segment length.

15. The method as claimed in claim 12, wherein the lower leg angle or thigh angle is directly measured using an inertial angle sensor, or is determined using an position sensor on a thigh or lower leg and a knee angle sensor.

16. The method as claimed in claim 15, wherein the length of the leg chord is determined from the knee angle and the thigh and lower leg segment lengths.

17. The method as claimed in claim 12, wherein the resistance is changed based on a direction of a change in at least one of the position and the length of the leg chord.

18. The method as claimed in claim 12, wherein a quotient is determined from a change in a position of the leg chord and a change in a thigh angle or lower leg angle, the quotient being used for an assessment of the walking situation.

19. The method as claimed in claim 12, wherein a quotient is determined from a change in a leg chord speed and a change in a thigh speed or a lower leg speed, the quotient being used for an assessment of the walking situation.

20. The method as claimed in claim 19, further comprising detecting forces in the lower part with a sensor during a stance phase or standing.

21. A method for controlling a change in resistance in an artificial joint of an orthosis, an exoskeleton, or prosthesis of a lower extremity, the method comprising:

providing an artificial joint having an upper part, a lower part, a resistance unit, and an adjustment device, the upper part being pivotally connected to the lower part, the resistance unit providing a flexion resistance or an extension resistance, the adjustment device including a control unit, the adjustment device being operable to change the flexion resistance or extension resistance if a sensor signal of the control unit activates the adjustment device;

changing the flexion resistance or extension resistance based on a length of a measured or calculated leg chord and derivatives thereof with respect to time, the leg chord being a connecting line between a hip center of rotation and a foot point, the hip center of rotation and the foot point being fixed relative to the upper part and the lower part, respectively.

* * * * *